US005204454A

United States Patent [19]

Rodenhouse et al.

[11] Patent Number: 5,204,454

[45] Date of Patent: Apr. 20, 1993

[54] PREPOLYMERIC POLYOLS CONTAINING MESOGENIC UNITS

[75] Inventors: Randall A. Rodenhouse, Pittsburgh, Pa.; Dittmar K. Nerger, Krefeld, Fed. Rep. of Germany; Douglas A. Wicks, Mt. Lebanon, Pa.

[73] Assignee: Miles Inc., Pittsburgh, Pa.

[21] Appl. No.: 732,566

[22] Filed: Jul. 19, 1991

[51] Int. Cl.[5] .................... C07C 245/06; C07C 69/76; C07C 229/00

[52] U.S. Cl. .................................... 534/805; 534/807; 534/810; 534/816; 534/823; 534/831; 534/839; 534/852; 560/63; 560/65; 560/66; 560/72; 560/73; 560/76; 560/83; 560/85; 560/35; 560/37; 560/60; 560/91; 560/92; 560/94; 560/96; 560/109; 556/432; 556/489

[58] Field of Search ....................... 560/60, 35, 37, 61, 560/62, 63, 65, 66, 72, 73, 76, 83, 85, 91, 92, 94, 96, 109; 534/805, 807, 810, 816, 823, 831, 839, 852; 556/432, 489

[56] References Cited

U.S. PATENT DOCUMENTS

| | | | |
|---|---|---|---|
| 4,412,059 | 10/1983 | Krigbaum et al. | 528/192 |
| 4,617,371 | 10/1986 | Blumstein et al. | 528/194 |
| 4,698,397 | 10/1987 | Toya et al. | 525/437 |
| 4,745,135 | 5/1988 | Thomas et al. | 521/114 |
| 4,798,849 | 1/1989 | Thomas et al. | 521/114 |

OTHER PUBLICATIONS

Liquid Crystal Polymers VII, W. J. Jackson et al pp. 307-326 1985, Journal of Applied Polymer Science: Applied Polymer Symposium.

*Primary Examiner*—José G. Dees
*Assistant Examiner*—Porfirio Nazario
*Attorney, Agent, or Firm*—Joseph C. Gil; Aron Preis

[57] ABSTRACT

Prepolymer polyols containing mesogenic moieties useful as reactants for the preparation of resinous materials are disclosed. Synthesized by condensing a polyether polyol with bifunctional mesogenic diacids, or diesters, the compounds of the invention are characterized by their reasonably low melt temperature which renders them suitable as additive materials in polymeric molding compositions and as precursors for the preparation of resinous materials.

The liquid crystalline properties of the prepolymers of the invention were found to depend on the type and molecular weight of the glycols and on the molar ratio between the glycols and the mesogenic reactant.

7 Claims, No Drawings

PREPOLYMERIC POLYOLS CONTAINING MESOGENIC UNITS

FIELD OF THE INVENTION

The invention related to prepolymeric polyols which contain mesogenic units in their molecular structure and more particularly to prepolymers which exhibit liquid crystalline properties.

SUMMARY OF THE INVENTION

Prepolymer polyols containing mesogenic moieties useful as reactants for the preparation of resinous materials are disclosed. Synthesized by condensing a polyether polyol with bifunctional mesogenic diacids or diesters. The compounds of the invention are characterized by their reasonably low melt temperature which renders them suitable as additive materials in polymeric molding compositions and as precursors for the preparation of resinous materials.

The liquid crystalline properties of the prepolymers of the invention were found to depend on the type and molecular weight of the glycols and on the molar ratio between the glycols and the mesogenic reactant.

BACKGROUND OF THE INVENTION

Liquid crystalline (mesogenic ) groups are moieties which can aggregate to form nematic, smectic or cholesteric ordering. The use of these compounds in the molecular structure of resinous materials has been proposed. It has for instance been proposed that the physical and barrier properties of polyurethanes may be improved by reacting a diisocyanate and/or polyisocyanate with a polyol containing mesogenic units.

The relevant art is noted to include "Liquid Crystal Polymers VII. Liquid crystalline polyesters of Trans-4,4'-stilbene dicarboxylic acid and aliphatic glycols" by W.J.Jackson, Jr. et al published in the Journal of Applied Polymer Science: Applied Polymer Symposium 41, 307-326 (1985), where a reaction of esters of trans-4,4'-stilbene dicarboxylic acid (SDA) with polymethylene glycols containing 4 to 10 methylene groups and several additional other glycols has been disclosed.

U.S. Pat. No. 4,412,059 disclosed a polymeric material comprising an optically active monomer. The material is said to be capable of forming a high modulus biaxially orientable structures of a cholesteric mesophase. Polymeric liquid crystals which retain their mesomorphic structure and properties at temperatures below the glass transition temperature are disclosed in U.S. Pat. No. 4,617,371. The polymers thus disclosed contain mesogenic and spacer units in alternating sequence. Relevant technology is also disclosed in U.S. Pat. No. 4,698,397 which relates to a cholesteric liquid crystal copolyester and in U.S. Pat. No. 4,745,135 which disclosed a polyol which contains liquid crystalline moieties. A significant difference between the present invention and the '135 document resides in the selection of the respective polyol systems. An organic bulk polymer containing microscopically dispersed therein liquid crystalline polymer has been disclosed in U.S.Pat. No. 4,798,849.

DETAILED DESCRIPTION OF THE INVENTION

In the synthesis of the prepolymer polyol of the present invention a mesogenic diacid or the corresponding diester conforming to

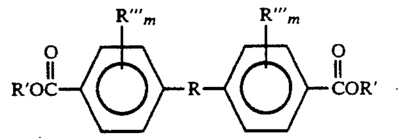

where R is, $-CH_2CH_2-$, $-CH=CH-$, $-C\equiv C-$, $-OCH_2-$, $-CO_2-$, $-CH=N-$, $-N=N-$ and where R' is $-H$, $-CH_3$, $-CH_2CH_3$ and where R''' denotes hydrogen, alkyl, alkyl aryl, aryl, alkyl ether, aryl ether, halogen, trialkyl silyl or trifluoromethane, and where m is 1 to 4, is condensed with at least one polyether polyol conforming to

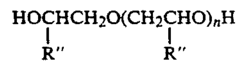

where R'' is at least one of $-H$ and $-CH_3$ and n is 0 to 45, preferably 0-22, most preferably 2-10. Importantly, the prepolymer polyol of the invention is imparted liquid crystalline properties by selecting a polyether polyol where R'' is hydrogen, n is about 1 to 4 and the mole ratio between the glycol and mesogenic reactants is about 2:1 to 9:8, preferably 3:2 to 9:8. most preferably 4:3 to 7:6.

The condensation reaction, in the presence of a suitable catalyst, is carried out at a temperature of about 240° C.

Suitable catalysts include titanium tetraisopropoxide, dibutyltin dilaurate and the acetates of manganese, cobalt, zinc, titanium, antimony, barium, calcium, magnesium and cadmium.

The preferred catalyst is titanium tetraisopropoxide.

The product of the reaction is characterized in that its molecular weight, as determined from the OH number, is about 356 to 4000, preferably 1000 to 2500 and in that it conforms structurally to

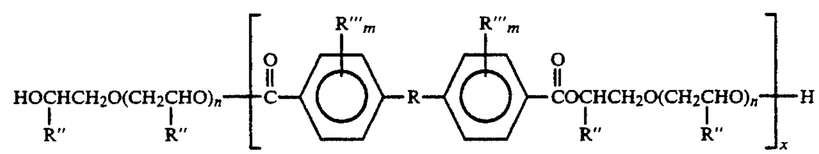

where x is an integer of 1 to 8, preferably 2 to 5 and where R, R'', R''', m and n are as noted above.

Importantly, the mole ratio between the polyether polyol and the mesogenic diester is in the range of from 2:1 to 9:8 preferably 3:1 to 6:5.

The prepolymer polyols of the invention are characterized in that they display a glass transition temperature in the range of about −40° C. to 0° C. and an isotropization temperature below 110° C. The prepolymer polyols , in some instances , are viscous oils having low glass transition temperatures and no apparent isotropization transition.

The prepolymer polyols of the invention may be branched by the incorporation of low concentrations of acids and/or esters having a functionality of at least three. The branching increases the functionality and depresses the ability of the polyols to crystallize.

The prepolymers of the invention are suitable as precursors in polyurethane formulations, including coatings, reaction injection molding and thermoplastic polyurethane formulations.

Experimental

In demonstrating the invention a flask equipped with a nitrogen gas inlet, a mechanical stirrer and a short distillation column was charged with 100 g (0.337 mole) of dimethyl trans-4,4'-stilbene dicarboxylate, 90 g (0.45 mole) of polyether conforming to $$HO-[CH_2CH_2O]_n-H$$

having a molecular weight of about 200 and an OH number of 561 and 100 ppm of titanium tetraisopropoxide. The ester interchange was carried out initially at 250° C. until a clear homogeneous solution resulted. The temperature was then reduced to 240° C. for 3 hours while methanol was being removed. The temperature was then reduced to 220° C. under reduced pressure (1 mm Hg) for about 1 hour until complete removal of methanol.

The characterization of the resulting prepolymer polyol was carried out by differential scanning calorimetry and by optically polarized microscopy. The prepolymer thus prepared had a Tg of −26° C. and a isotropization temperature of 51° C.

The molecular weight of the prepolymer was determined to be 1493.

Additional prepolymer polyols were prepared following substantially the same procedure as described above. In all the examples, the results of which are summarized in the table below, the mesogenic unit derived from dimethyl trans-4,4'-stilbene dicarboxylate, and the catalyst which was used in each case is noted in the table. The molar amounts of the mesogenic reactant and the type and molar amounts of the polyols varied as described below.

The characteristics of the resulting prepolymer are shown below.

| Example | catalyst | molar amount mesogen | Polyether polyol type and molar amount | Prepolymer MW[1] | Prepolymer properties |
|---|---|---|---|---|---|
| 1 | Sn | 1.25 | PEO3 1.50 | (2180) | Tg = −11° C.<br>Ti[3] = 82° C.<br>LC[2] |
| 2 | Sn | 1.31 | DiPG 1.57 | (1965) | not LC, solid |
| 3 | Sn | 0.338 | TriPG 0.414 | (2312) | not LC, solid |
| 4 | Sn | 1.25 | TriEG 1.50 | (2060) | Tg = 4° C.<br>Ti = 102° C.<br>LC |
| 5 | Sn | 1.25 | TetraEG 1.56 | (2324) | Tg = −12° C.<br>Ti = 103° C.<br>LC |
| 6 | Sn | 0.338 | TriEG/TetraEG<br>50:50 0.485 | (1342)<br>(1342) | Tg = −26° C.<br>Ti = 64° C.<br>LC |
| 7 | Sn | 1.25 | TriEG/TetraEG<br>50:50 1.50 | (2192)<br>(2192) | Tg = −10° C.<br>Ti = 77° C.<br>LC |
| 8 | Sn | 0.74 | PPG1 0.99 | 2266 | thick oil<br>not LC<br>Tg = −17° C. |
| 9 | Tip | 2.25 | PPG1 3.00 | 2061 | Thick oil<br>not LC<br>Tg = −34° C. |
| 10 | Sn | 0.25 | PPG9 0.50 | (2389) | oil<br>not LC |
| 11 | Tip | 0.338 | PEO4 0.41 | 2032 | Tg = −17° C.<br>Ti = 50° C.<br>LC |
| 12 | Sn | 0.905 | PEO4 1.09 | 1563 | Tg = −22° C.<br>Ti = 51° C.<br>LC |
| 13 | Sn | 0.50 | PEO4 0.625 | (2030) | Tg = −10° C.<br>Ti = 59° C.<br>LC |

[1]the number in parentheses is the calculated molecular weight, other molecular weight numbers were determined from the OH number.
[2]LC = liquid crystalline properties
[3]isotropization temperature
EG—ethylene glycol
PG—propylene glycol
PEO—polyethylene glycol
PPG—polypropylene glycol
PEO3—PEO having a molecular weight of 165
PEO4—PEO having a molecular weight of 200
PPG9—PPG having a molecular weight of 1000
PPG1—PPG having a molecular weight of 425
Sn = dibutyl tin dilaurate
Tip = titanium tetraisopropoxide The following is a summary of additional experiments which were carried out on branched systems. In these examples, the catalyst used was titanium tetraisopropoxide. The branching agent was 0.034 moles of trimethylbenzenetricarboxylate (TMBTC); in example 14 the branching agent was 1,3,5-TMBTC, and in Example 15 the branching agent was 1,2,4-TMBTC.

| Example | molar amount mesogen | Polyether polyol type and molar amount | | OH number | prepolymer properties |
|---|---|---|---|---|---|
| 14 | 0.304 | PEO4 | 0.47 | 79.2 | LC under shear Tg = −23° C. |
| 15 | 0.304 | PEO4 | 0.47 | 80.7 | LC under shear Tg = −22° C. |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A prepolymer conforming structurally to

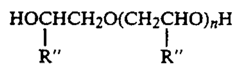

where x is an integer of 1 to 8, R is, —$CH_2CH_2$—, —CH═CH—, —C≡C—, —$OCH_2$—, —$CO_2$—, —CH═N—, —N═N— and n is 0 to 45, R‴ denotes hydrogen, alkyl, alkyl aryl, alkyl ether, aryl ether, halogen, trialkyl silyl or trifluoromethane R″ denotes at least one of —H and —$CH_3$ and m is 1 to 4.

2. The prepolymer of claim 1 further characterized in that it has a glass transition temperature in the range of about −40° C. to 0° C. and an isotropization temperature below 110° C.

3. The prepolymer of claim 1 wherein said n is 0 to 22.

4. The prepolymer of claim 1 wherein said n is 2 to 10.

5. The prepolymer of claim 1 wherein said R″ is H and n is 1–4.

6. The prepolymer of claim 1 wherein said R″ is H, n is 1–4, and x is 2 to 5.

7. A process for preparing a prepolymer conforming structurally to

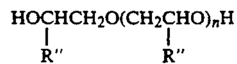

wherein x is 1 to 8 comprising reacting a mesogenic diacid or the corresponding diester conforming to

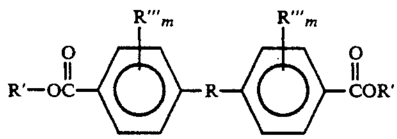

where R is, —$CH_2$—$CH_2$, —CH═CH—, —C≡C—, —$OCH_2$—, —$CO_2$—, —CH═N—, —N ═N— and where R′ is —H, —$CH_3$, —$CH_2CH_3$, R‴ denotes halogen, alkyl, alkyl aryl, aryl, alkyl ether, aryl ether, halogen, trialkyl silyl or trifluoromethane and m is 1 to 4, with at least one polyether polyol conforming to

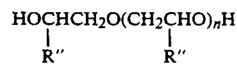

where R″ is at least one of hydrogen and $CH_3$ group, and n is 0 to 45 in the presence of dibutyltin dilaurate as a catalyst.

* * * * *